(12) United States Patent
Han et al.

(10) Patent No.: US 11,244,743 B2
(45) Date of Patent: *Feb. 8, 2022

(54) ADAPTIVE WEIGHTING OF SIMILARITY METRICS FOR PREDICTIVE ANALYTICS OF A COGNITIVE SYSTEM

(71) Applicant: International Business Machines Corporation, Armonk, NY (US)

(72) Inventors: Yanyan Han, San Jose, CA (US); Sheng Hua Bao, San Jose, CA (US); Xiaoyang Gao, San Jose, CA (US); Brian S. Dreher, San Jose, CA (US); William S. Spangler, San Martin, CA (US); Feng Wang, Santa Clara, CA (US)

(73) Assignee: International Business Machines Corporation, Armonk, NY (US)

( * ) Notice: Subject to any disclaimer, the term of this patent is extended or adjusted under 35 U.S.C. 154(b) by 831 days.

This patent is subject to a terminal disclaimer.

(21) Appl. No.: 15/862,902

(22) Filed: Jan. 5, 2018

(65) Prior Publication Data

US 2019/0213303 A1 Jul. 11, 2019

(51) Int. Cl.
*G16C 20/40* (2019.01)
*G06N 20/00* (2019.01)
(Continued)

(52) U.S. Cl.
CPC ............. *G16C 20/40* (2019.02); *G06N 20/00* (2019.01); *G16C 20/30* (2019.02); *G16C 20/70* (2019.02); *G10L 15/18* (2013.01); *G16B 40/00* (2019.02)

(58) Field of Classification Search
CPC ........ G16C 20/40; G16C 20/30; G16C 20/70; G06N 20/00; G17B 40/00; G10L 15/18
(Continued)

(56) References Cited

U.S. PATENT DOCUMENTS 7,472,121 B2    12/2008  Kothari et al.
8,706,427 B2 *   4/2014  Haque ................... G16C 20/40
                                                          702/32
(Continued)

FOREIGN PATENT DOCUMENTS

CA    2764496 A1      12/2010
EP    1840695 A2 *   10/2007   ............ G06Q 10/00
EP    1840695 A3 *   10/2007   ............ G06Q 10/00

OTHER PUBLICATIONS

List of IBM Patents or Patent Applications Treated as Related, filed Jun. 18, 2019.

*Primary Examiner* — Alexey Shmatov
*Assistant Examiner* — Robert Bejcek, II
(74) *Attorney, Agent, or Firm* — Will Stock; Edell, Shapiro & Finnan, LLC

(57) ABSTRACT

According to embodiments of the present invention, similarity metrics or measures of similarity may be combined using an adaptive weighting scheme. A subset of entities from a first set of entities that have a known relationship is randomly selected. The subset is combined with a second set of entities that have an unknown relationship to each other and/or to the first set of entities. At least two different measures of similarity (similarity metrics) between the first set and the combined second set (including the subset) is determined for each entity in the second set. For each entity in the second set, the at least two different measures of similarity are compared, and a weight is assigned adaptively to each measure of similarity based on the magnitude of the measure of similarity. The weighted measures of similarity are combined to determine an aggregate adaptively weighted similarity score for each entity.

12 Claims, 6 Drawing Sheets

(51) Int. Cl.
*G16C 20/30* (2019.01)
*G16C 20/70* (2019.01)
*G10L 15/18* (2013.01)
*G16B 40/00* (2019.01)

(58) Field of Classification Search
USPC .......................................................... 706/12
See application file for complete search history.

(56) References Cited

U.S. PATENT DOCUMENTS

| | | |
|---|---|---|
| 9,747,279 B2 | 8/2017 | Boies et al. |
| 9,753,968 B1 * | 9/2017 | Ronen .................... G16H 50/70 |
| 10,019,442 B2 * | 7/2018 | Nefedov ................. G06F 16/93 |
| 10,713,321 B1 | 7/2020 | Wen et al. |
| 2007/0143322 A1 * | 6/2007 | Kothari ................. G06F 40/194 |
| 2011/0213567 A1 | 9/2011 | Haque et al. |
| 2016/0350294 A1 | 12/2016 | Nefedov et al. |
| 2017/0255669 A1 * | 9/2017 | Ronen .................... G16H 10/60 |
| 2017/0293696 A1 * | 10/2017 | Bendersky .......... G06F 16/9024 |
| 2019/0294667 A1 | 9/2019 | Aratsu et al. |
| 2019/0304573 A1 | 10/2019 | Han et al. |

* cited by examiner

ADAPTIVE WEIGHTING OF SIMILARITY METRICS FOR PREDICTIVE ANALYTICS OF A COGNITIVE SYSTEM

BACKGROUND

1. Technical Field

Present invention embodiments relate to predictive analytics, and more specifically, to adapting weights to particular sets of inputs as part of a predictive analytics scheme for a cognitive system.

2. Discussion of the Related Art

In the modern computing era, computational techniques and systems allow for complex analysis on large volumes or corpuses of data. Cognitive and machine learning systems in combination with natural language processing techniques may be used to extract, analyze and make inferences or predictions from large sets of complex data.

Multiple types of analytics may be performed to determine similarities between elements of data sets. However, determining how to combine different similarity metrics to improve predictive capability is often complex and difficult. For example, using a random weighting scheme in which each similarity metric is assigned a random weight, or an equal weighting scheme in which the same weight is assigned to each similarity metric frequently undermines the true similarity between entities and does not reflect the true relationship between the entities. Both of these weighting schemes may lead to inaccurate or false predictions.

SUMMARY

According to an embodiment of the present invention, similarity metrics or measures of similarity may be combined using an adaptive weighting scheme based on particular inputs.

A subset of entities from a first set of entities that have a known relationship is randomly selected. The subset is combined with a second set of entities that have an unknown relationship to the first set of entities. At least two different measures of similarity (similarity metrics) between the first set and the combined second set (including the subset) is determined for each entity in the combined second set. For a given entity in the second set, the at least two different measures of similarity are compared, and a weight is assigned adaptively to each measure of similarity based on the respective magnitude of the measure of similarity. The weighted measures of similarity are combined to determine an aggregate adaptively weighted similarity score for the entity.

It is to be understood that the Summary is not intended to identify key or essential features of embodiments of the present disclosure, nor is it intended to be used to limit the scope of the present disclosure. Other features of the present disclosure will become easily comprehensible through the description below.

BRIEF DESCRIPTION OF THE DRAWINGS

Generally, like reference numerals in the various figures are utilized to designate like components. Through the more detailed description of some embodiments of the present disclosure in the accompanying drawings, the above and other features and advantages of the present disclosure will become more apparent.

DETAILED DESCRIPTION

Figure 1:
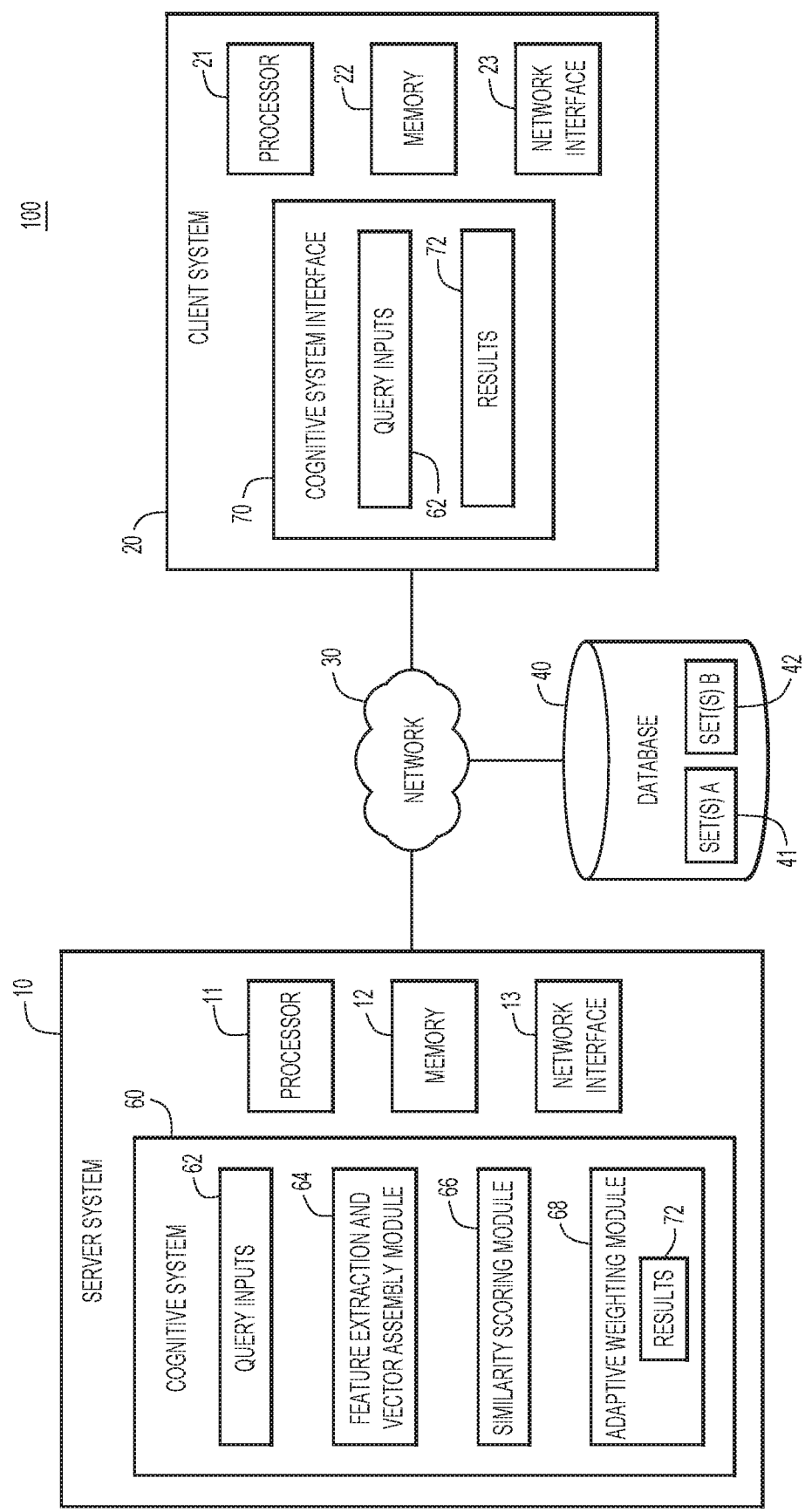
FIG. 1 is a block diagram of an example computing environment for adaptive weighting of similarity metrics in accordance with embodiments of the present disclosure.

An example environment for use with present invention embodiments is illustrated in FIG. 1. Specifically, the environment includes one or more server systems 10, and one or more client or end-user systems 20. Server systems 10 and client systems 20 may be remote from each other and may communicate over a network 30. The network may be implemented by any number of any suitable communications media (e.g., wide area network (WAN), local area network (LAN), Internet, Intranet, etc.). Alternatively, server systems 10 and client systems 20 may be local to each other, and may communicate via any appropriate local communication medium (e.g., local area network (LAN), hardwire, wireless link, Intranet, etc.).

Client systems 20 enable users to submit queries (e.g., queries for predictive analytics, etc.) to server systems 10 to generate predictions based upon an analysis of a large corpus of data (e.g., scientific data, scientific journals, publically and/or privately accessible chemical databases, databases of known pharmaceutical and/or biologic therapeutic compounds, databases/literature of known genes/DNA, databases/literature of expressed RNA, databases/literature covering proteomics, databases/literature covering metabolomics, etc.). In some aspects, users can input query terms, e.g., lung cancer genes, drugs to treat diabetes, etc.), and the system 100 will return a list of ranked entities, predicted to be related to the query based on a plurality of similarity metrics that have been adaptively weighted. In general, the highest ranked entity (highest aggregate similarity score) will be presented at the top of the list, with subsequent entities presented in an order of descending adaptively weighted aggregate similarity scores.

The server systems 10 include a cognitive system 60 to generate predictions based upon analysis of a large corpus of data. A database system 40 may store various types of information for the analysis (e.g., set(s) A 41 and set(s) B 42). Set(s) A 41 are groups of entities (e.g., gene names, chemical compounds/names, protein names, etc.) that have a known relationship. For example, a set A may contain a list of genes related to lung cancer. Another set A may include a list of chemical compounds that are fluoroquinolones. Typically, the relationship between the entities in a particular set A has been verified. Set(s) B 42 are groups of entities that have an unknown relationship to each other and/or to set A.

Database 40 may also store feature vectors, generated by feature extraction and vector assembly module 64, associated with each entity, which describes the characteristics of the entity and/or the context of the entity within the corpus of documents. The database system 40 may be implemented by any conventional or other database or storage unit, may be local to or remote from server systems 10 and client systems 20, and may communicate via any appropriate communication medium (e.g., local area network (LAN), wide area network (WAN), Internet, hardwire, wireless link, Intranet, etc.).

Server systems 10 and client systems 20 may be implemented by any conventional or other computer systems preferably equipped with a display or monitor, a base (e.g., including at least one hardware processor 11, 21 (e.g., microprocessor, controller, central processing unit (CPU), etc.), one or more memories 12, 22 and/or internal or external network interfaces or communications devices 13, 23 (e.g., modem, network cards, etc.)), optional input devices (e.g., a keyboard, mouse or other input device), and any commercially available and custom software (e.g., server/communications software, browser/interface software, etc.). Server system 10 comprises cognitive system 60, which includes query inputs 62, feature extraction and vector assembly module 64, similarity scoring module 66, and adaptive weighting module 68 as described herein. Results 72 comprise a ranked list of entities in response to a user query. The client systems 20 may present a graphical user (e.g., GUI, etc.) or other cognitive system interface 70 (e.g., command line prompts, menu screens, etc.) to solicit information from users pertaining to the desired analysis, and may provide reports (e.g., lists, spreadsheets, etc.) including analysis results 72 (e.g., predictive analytics including ranked entities corresponding to the query, individual similarity scores (e.g., drug, chemical, text, etc.), adaptively weighted similarity scores, aggregate adaptively weighted similarity scores, etc.).

Alternatively, one or more client systems 20 may analyze a corpus of documents to generate predictive analytics (e.g., a ranking of entities generated in response to a query, ranked according to an aggregate of adaptively weighted similarity scores, etc.) when operating as a stand-alone unit. In a stand-alone mode of operation, the client system stores or has access to the data (e.g., data stored on database 40), and includes a cognitive system 60 to generate predictive analytics. The graphical user (e.g., GUI, etc.) or other interface 70 (e.g., command line prompts, menu screens, etc.) solicits information from a corresponding user pertaining to the desired documents and analysis, and may provide reports including analysis results 72.

Cognitive system 60 may include one or more modules or units to perform the various functions of present invention embodiments described herein. The various modules (e.g., query inputs 62, feature extraction and vector assembly module 64, similarity scoring module 66, and adaptive weighting module 68, etc.) may be implemented by any combination of any quantity of software and/or hardware modules or units, and may reside within memory 12 of the server for execution by processor 11.

Query inputs 62 may include query terms provided by the user. The query terms may be utilized to select one or more data set(s) A 41, which have a known relationship. For instance, if a user queries colon cancer genes, then a data set A including a plurality of genes known to be involved in the development and/or progression of colon cancer may be selected. Set B, involving entities with an unknown relationship to each other and/or to data set A, may also be selected by the cognitive system 60 for analysis.

Feature extraction and vector assembly module 64 generates vectors describing the characteristics of the entities from analysis of the corpus of data. For example, the feature extraction and vector assembly module 64 may include information which links an entity to the development and progression of particular diseases, to the treatment of particular diseases, to particular chemical structures, etc. In some embodiments, feature extraction and vector assembly module 64 may be integrated with the similarity scoring module 66, while in other embodiments, the feature extraction and vector assembly module 64 may act as a separate module which provides feature vectors to the similarity scoring module 66 for analysis.

Similarity scoring module 66 computes a similarity score for each type of similarity metric, or measure of similarity. For example, similarity scoring module may compute: a chemical similarity using a chemicalSimilarity function; a text similarity using a textSimilarity function; or a drug similarity using a drugSimilarity function. These functions are described throughout the application.

Each of the outputs from the similarity scoring module may be provided to the adaptive weighting module 68, which weights the measures of similarity based upon their respective magnitude. The adaptive weighting scheme is described in additional detail throughout the application. Results 72 from the adaptive weighting module (e.g., individual similarity scores, adaptively weighted similarity scores, aggregate adaptively weighted similarity (AAWS) scores, a listing of entities that are ranked according to the aggregate adaptively weighted similarity scores, etc.) may be provided to the user, via the cognitive system interface 70.

Figure 2:
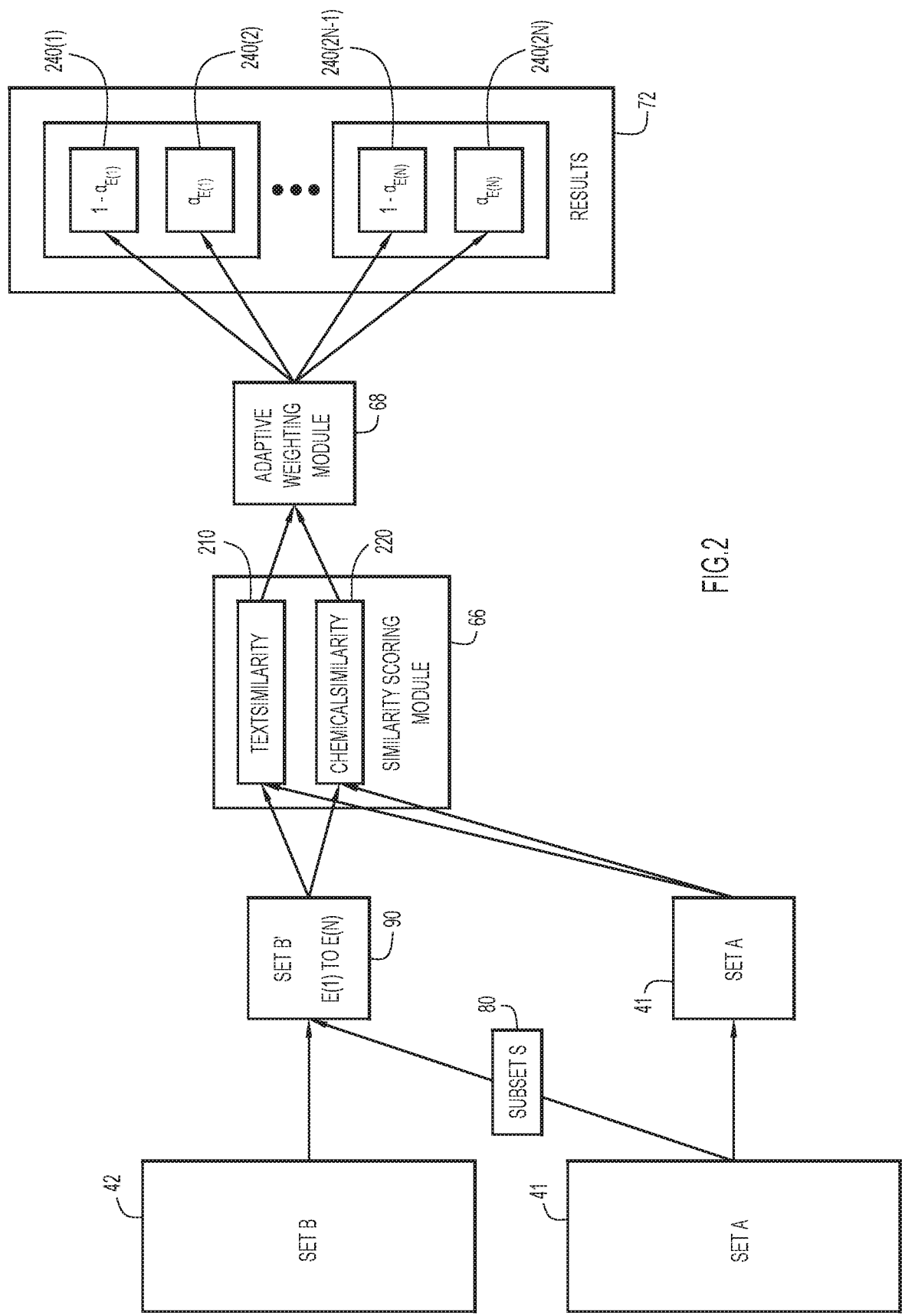
FIG. 2 is an illustration showing adaptive weighting with two similarity metrics, in accordance with embodiments of the present disclosure.

FIG. 2 shows an example embodiment of determining an adaptively weighted similarity score using a combination of two different similarity metrics that are adaptively weighted based upon a set of inputs. Set A 41 may include entities that have a known relationship. In some aspects, this may include chemical names, gene names, or scientific terms, etc. that are related to each other, e.g., based on a similar structure, implicated in a particular disease, etc. In some embodiments, set A 41 has been curated to verify the relationship among the entities in this group. As an example, set A may include genes related to a certain type of cancer, such as breast cancer, pancreatic cancer, or colon cancer, etc. In another embodiment, set A may include categories of chemicals, for instance, a set of compounds that are each classified as a type of benzodiazepine or a type of fluoroquinolone.

Set B 42 may include a random sampling of entities in which the relationship between the entities is not known. In some aspects, set B 42 may include chemical names, gene names, or scientific terms, etc.

To determine a similarity measure between an entity in set A and an entity in set B, a subset of A is combined with set B. Set A and combined set B (referred to as B' or B prime) are analyzed by a plurality of similarity functions. The respective individual similarity scores are adaptively weighted and combined to generate an aggregate adaptively weighted similarity (AAWS) score. This approach provides a more realistic measure of the true similarity between entities in set A and set B, than traditional weighting schemes, which may assign weights uniformly or randomly, or may not combine similarity metrics at all.

In this particular example, a random subset of entities in input set A is selected to create subset S 80. Subset S 80 is combined with input set B 42 to form a combined set B' 90 with elements E(1) to E(N). The two sets (set A 41 and set B' 90) are then analyzed by the similarity scoring module 66.

A first similarity measure, textSimilarity 210, may be used to determine a similarity between entities based on the context of a term in a document, etc. Text similarity may evaluate a corpus of documents that mentions a particular entity, e.g., a particular chemical name, a particular gene name, a disease type, or other characteristic, etc. to determine a similarity score based on contextual analysis. This function may consider the context of an entity (e.g., what the document, which may be a publication, a literature reference, or a database, discloses about the particular entity). In some aspects, a document may be represented by a feature vector, a vector of terms which describe the document. The text similarity function may compare, using feature vectors, documents comprising particular entities across a corpus of documents, to determine a similarity score for an entity in set B/B' relative to set A.

Another type of similarity score, chemicalSimilarity 220, may be used to determine a similarity score based on chemical structure. The chemical similarity may be evaluated based on chemical structure/connectivity of atoms, the number of atoms, the types of atoms, the chemical bonds, chemical backbones, functional side groups, etc. The chemical similarity may be computed across of corpus of chemical structures, identified in a corpus of documents, to determine a similarity score for an entity in set B/B' relative to set A.

These functions, textSimilarity 210 and chemicalSimilarity 220, may be used to generate a text-based similarity score and a chemical-based similarity score for each entity in set B', which includes computing similarity scores for each entity in subset S.

These scores are fed into adaptive weighting module 68, where the weights are adjusted based upon the respective magnitudes of the similarity scores and rankings, corresponding to the particular sets of inputs (e.g., set A and set B'). The type of similarity score having a higher value and/or associated with an entity having a higher rank will be assigned a weight $\alpha$, while the other type of similarity score having a lower value and/or associated with an entity having a lower rank will be assigned a weight $(1-\alpha)$. Here, it is presumed that $\alpha > 1-\alpha$, so that the higher scoring similarity metric will be weighted more than the lower scoring similarity metric.

In some embodiments, the weights $\alpha$ and $(1-\alpha)$ are determined by normalizing the similarity scores. For example, if the text similarity score is 0.2 and the chemical similarity score is 0.6, then the normalized weights may be computed as 0.2/0.8=0.25 and 0.6/0.8=0.75. Thus, in some embodiments, $\alpha$ may reflect the relative weight of the two similarity values, and may be a value proportional to the two similarity values.

For example, if the chemicalSimilarity score is higher than the textSimilarity score, then the chemicalSimilarity score will be assigned a weight that is higher than the weight for the textSimilarity score. Thus, a weight $\alpha$ will be assigned to the chemicalSimilarity score and a weight $(1-\alpha)$ will be assigned to the textSimilarity score, where $\alpha > (1-\alpha)$. This will ensure that the chemical similarity is weighted more heavily than the text similarity for a particular entity, and thus, is more reflective of the true nature of the relationship between the entities.

A set of scores are shown in this example with weights 240(1) and 240(2), corresponding to text and chemical similarity scores for an entity (E(1)) in set B'. Similarly, weights 240(2N-1) and 240(2N) correspond to weights for the Nth entity in set B'. An aggregate adaptively weighted similarity (AAWS) score for a particular entity may be generated according to the following formula:

$$\text{AAWS score} = \alpha * \text{similarityScore1} + (1-\alpha) * \text{similarityScore2} \quad (1)$$

Here, similarityScore1 is the type of similarity score highest in magnitude of two types of similarity scores, and similarityScore2 is the type of similarity score lowest in magnitude of two types of similarity scores.

Figure 3:
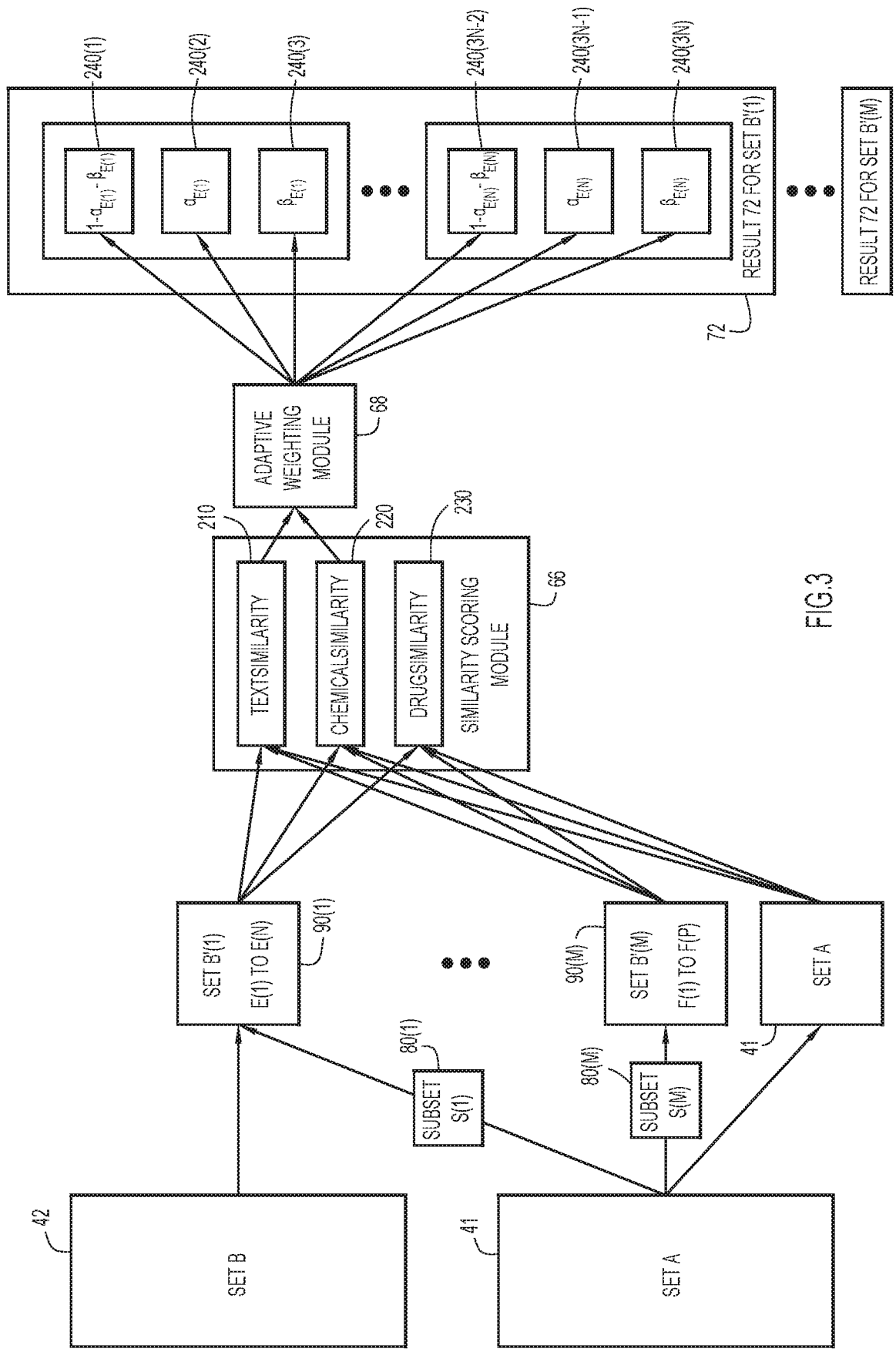
FIG. 3 is an example of determining scores for three similarity metrics and with multiple subsets, according to embodiments of the present disclosure.

Referring to FIG. 3, in another example embodiment, an adaptively weighted similarity score is determined using a combination of three different similarity metrics that are adaptively weighted based upon a particular set of inputs. These similarity metrics are text similarity, chemical similarity, and drug similarity, and may be combined into an aggregate adaptively weighted similarity (AAWS) score for a particular entity.

Similar to the previous example, set A 41 includes entities that have a known relationship, and may have been curated to verify the relationship among the entities in this group. Set B 42 may include a random set of terms in which the relationship between the terms is not known.

As the adaptively weighted similarity scores depend upon inputs, in some embodiments, cross validation may be performed to minimize random noise in AAWS scores from random selection of terms in A to include in B. To perform cross validation, multiple sets S, e.g., S(1) 80(1) . . . S(M) 80 (M), may be generated. In some aspects, all entities in set A may be included in one or more sets S. Similar to the previous example, a set S is added to set B to generate a combined set B' for evaluation. Set B' and set A are provided to the similarity functions to generate similarity scores for each type of function, which are then provided to the adaptive weighting module 68 to generate AAWS scores.

In an embodiment, once the plurality of sets (e.g., set A with set B'(1), set A with set B'(2), . . . set A with B'(M)) have been evaluated, the AAWS scores may be combined (e.g., averaged, etc.) to reach a combined AAWS similarity. The number (M) of sets S to generate may be determined by evaluating the convergence of a similarity score(s). When the similarity score(s) show convergence to a given value (e.g., based on a statistical metric), then generation of additional sets S and evaluation of additional combined sets B' may terminate.

On the other hand, if similarity score(s) do not suitably converge, then the similarity metric may be omitted and a notification may be provided to the user indicating that a prediction cannot be reliably made.

Accordingly, in this example, a plurality of random sets S(1) . . . S(M) of entities from set A are combined with set B to form sets B'(1) to B'(M), respectfully. Each pair of sets, e.g., set B'(1) and set A, set B'(2) and set (A), . . . set B'(M) and set A, are then analyzed by the three (or more) similarity measures.

In this example, a first similarity measure, textSimilarity 210, may be used to determine a similarity based on text-based analytics. A second similarity, chemicalSimilarity 220, may be used to determine a similarity based on chemical structure. A third similarity, drugSimilarity 230, may be used to determine a similarity between therapeutic drugs. Each of these functions, textSimilarity 210, chemicalSimilarity 220, and drugSimilarity 230, generates a different type of similarity score for each entity in input set B'. These scores are fed into adaptive weighting module 68, where the weights are adjusted based upon the similarity scores for these particular sets of inputs. For example, if the chemicalSimilarity score is higher than the textSimilarity score, and the textSimilarity score is higher than the drugSimilarity score, then the chemicalSimilarity score will be assigned a weight that is higher than the weight for the textSimilarity score, and the textSimilarity score will be assigned a weight that is higher than the weight for the drugSimilarity score. For example, a weight $\alpha$ will be assigned to the chemicalSimilarity score, a weight $\beta$ will be assigned to the textSimilarity score, and a weight $(1-\alpha-\beta)$ will be assigned to the drugSimilarity score, where $\alpha>\beta>(1-\alpha-\beta)$. This will ensure that chemical similarity is weighted more heavily than the textSimilarity score, and that the textSimilarity score is weighted more heavily than the drugSimilarity score for a particular entity, and thus, will be reflective of the true nature of the data. In some embodiments, the text, drug, and chemical similarity scores may be normalized to generate the respective weights.

This type of adaptive weighting may be extended to any number of different types of similarity scores. In some embodiments, the weights are normalized, such that the sum of the individual weights equals one.

Results 72 show a set of scores with weights 240(1) ... 240(3N). The scores for a particular entity may be combined as follows:

$$\text{AAWS score} = \alpha * \text{similarityScore1} + \beta * \text{similarityScore2} + (1-\alpha-\beta) * \text{similarityScore3} \quad (2)$$

Here, similarityScore1 is the similarity score highest in magnitude of three types of similarity scores, and similarityScore3 is the similarity score lowest in magnitude of three types of similarity scores.

Thus, in FIGS. 2 and 3, the weight is determined by moving some of the entities (a change set) in set A to set B, creating a combined set B' and calculating similarity scores for this combined set. Because different sets may generate different scores for similarity metrics, the weights are adaptive to the inputs, e.g., due to variability in the respective change set.

The similarity score and ranking for each entity in set S is expected to be higher than the entities in original set B, or at least, the entities in set S are projected to be among the top K (where K is comparably small relative to the size of the entire set B'). The entities in set S have a known relationship with the entities in set A, and therefore, the presence of this relationship is reflected in the similarity score and ranking.

Figure 4:
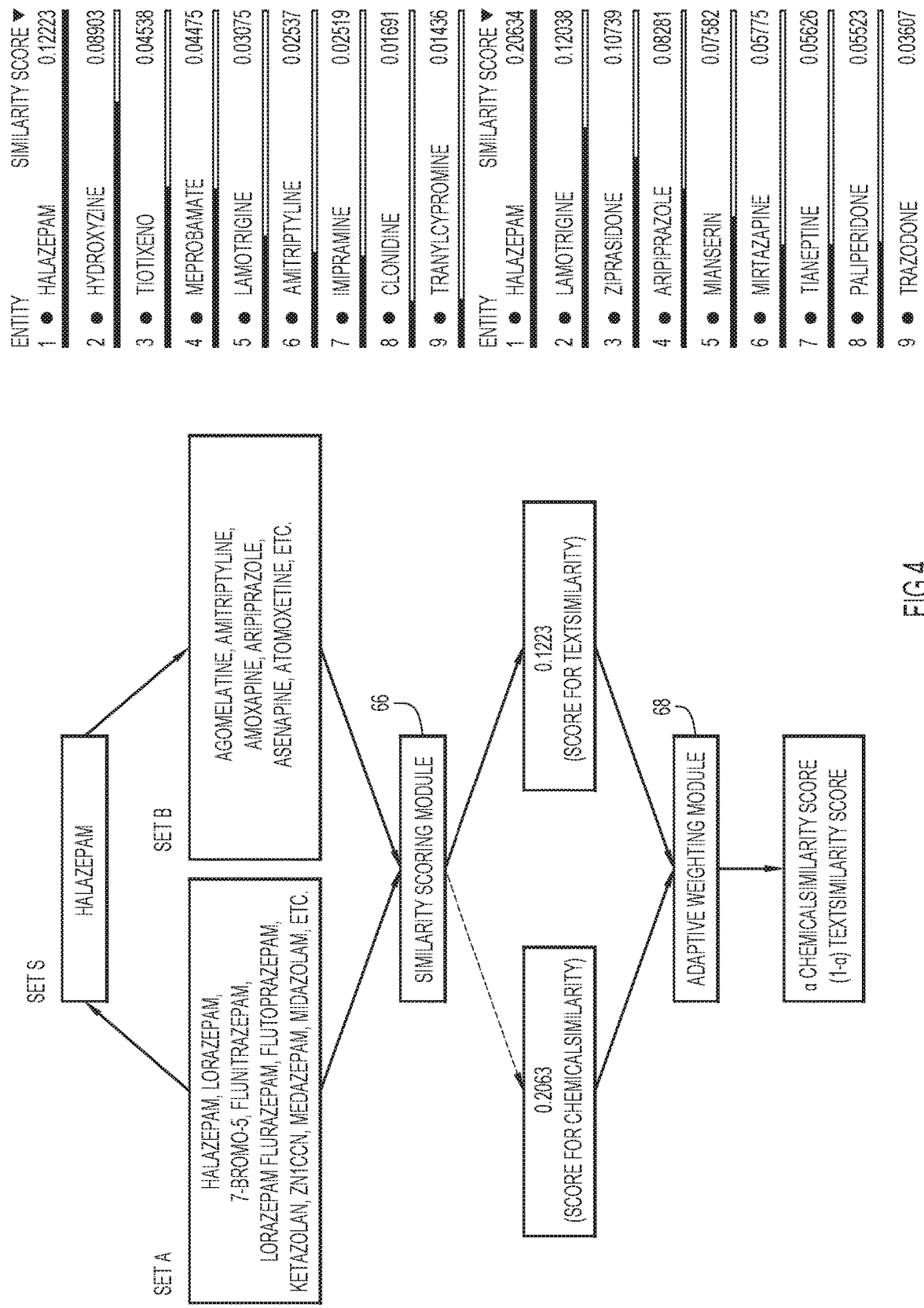
FIG. 4 is an example of applying adaptive weighting to similarity metrics for an entity that is a chemical name, according to embodiments of the present disclosure.

FIG. 4 shows an example computation according to the techniques provided herein. Set A includes a variety of chemical names, which are in a class of compounds known as benzodiazepines. In this example, set S consists of a single compound, halazepam, which is combined with set B to generate set B' (not shown). Sets A and B' are fed into the similarity scoring module 66, which generates a chemical similarity score and a text similarity score for each entity in B'. In this example, a chemicalSimilarity score of 0.2063 and a textSimilarity score of 0.1223 were generated for halazepam. These scores are provided to adaptive weighting module 68, wherein the chemicalSimilarity score will be assigned a higher weight than the textSimilarity score, since the chemicalSimilarity score has the same ranking for halazepam but with a higher similarity score.

Figure 5:
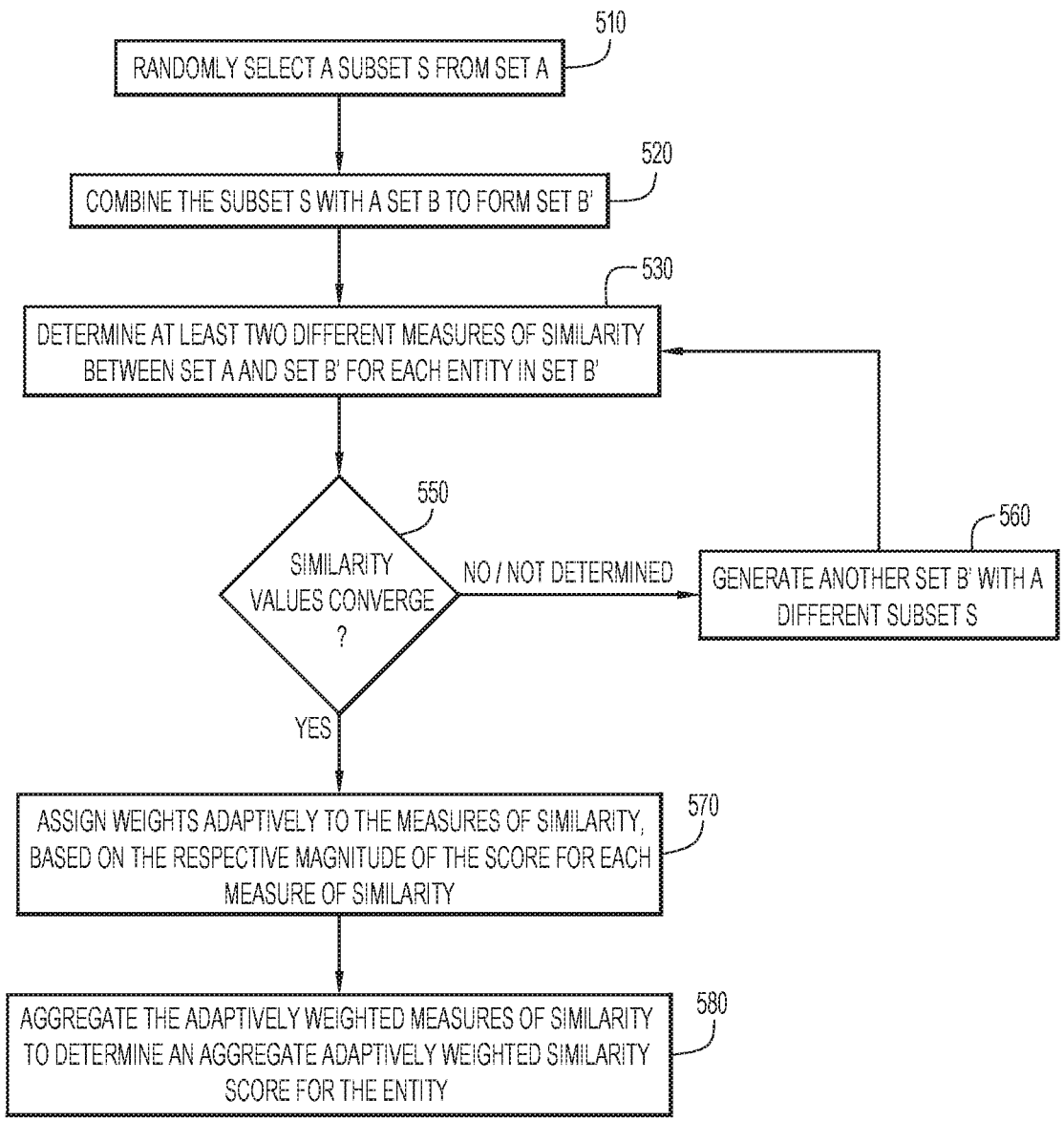
FIG. 5 is a flowchart of operations for applying adaptive weighting, with cross validation, to particular sets of inputs, according to embodiments of the present disclosure.

FIG. 5 is a flow diagram showing operations of determining an AAWS score, including cross validation, according to an embodiment of the present invention. At operation 510, a subset S is randomly selected from set A. At operation 520, the subset S is combined with a set B to form set B'. At operation 530, at least two different measures of similarity between set A and set B' are determined for each entity in set B'. At operation 550, a determination is made as to whether the similarity values have converged. If the similarity values have not converged (or convergence has not been yet determined), then at operation 560, another set B' with a different subset S is generated, and the process repeats, beginning at operation 530. If the similarity values have converged, the process continues to operation 570, wherein weights are assigned adaptively to the measures of similarity, based on the respective magnitude of the score for each measure of similarity, and adapted to the respective set S. At operation 580, the adaptively weighted measures of similarity are aggregated to determine an aggregate adaptively weighted similarity score for the entity.

In this example, it is understood that operation 550 may occur after operation 530, after operation 570, or after operation 580. Convergence may be evaluated for the individual similarity values, for the adaptively weighted similarity values, or for the aggregated adaptively weighted similarity values.

Improved techniques are provided herein for combining similarity metrics using adaptive weighting. By adapting weights for similarity metrics based on the current set of inputs, e.g., set A and set B', the true relationship between the input sets may be more accurately represented.

Figure 6:
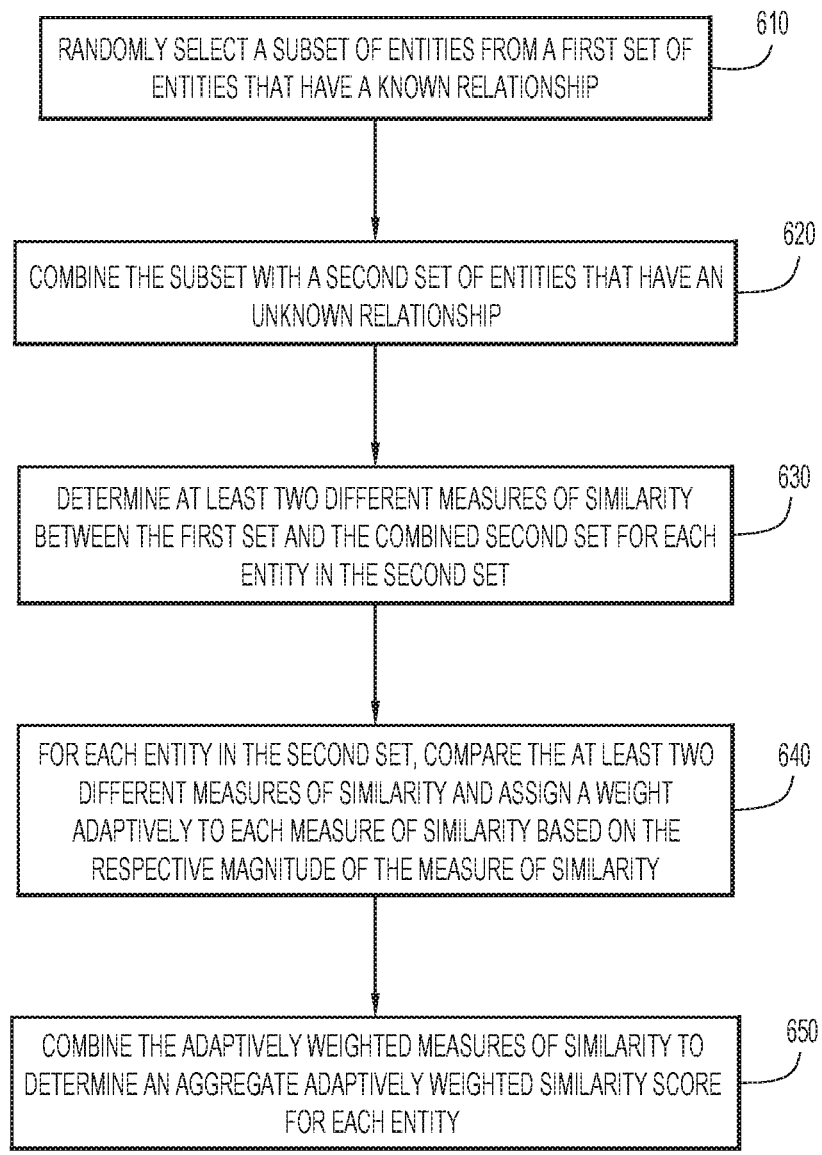
FIG. 6 is a flowchart of operations for generally applying adaptive weighting to similarity metrics, according to embodiments of the present disclosure.

FIG. 6 is a flow diagram showing general operations of determining AAWS scores, according to embodiments of the present invention. At operation 610, a subset of entities is randomly selected from a first set of entities that have a known relationship. At operation 620, the subset is combined with a second set of entities that have an unknown relationship to the first set of entities. At operation 630, at least two different measures of similarity between the first set and the combined second set are determined for each entity in the second set. At operation 640, for each entity in the second set, the at least two different measures of similarity are compared, and a weight is assigned adaptively to each measure of similarity based on the respective magnitude of the measure of similarity. At operation 650, the weighted measures of similarity are combined to determine an aggregate adaptively weighted similarity score for each entity.

Accordingly, present invention embodiments may be used as part of a predictive analytics system and/or methodology to generate predictions based upon the analysis of a corpus of information. Predictive analytics may be used to identify molecules (e.g., nucleotides including genes, RNA, proteins, etc.) involved in the formation and/or progression of a disease or disorder (e.g., cancer, metabolic disorders, neurologic disorders, etc.) as well as drugs (e.g., a chemical molecule, a protein, an antibody, etc.) that may be useful in treating said diseases or disorders.

For example, a user may wish to predict genes involved in the formation of lung cancer in order to identify new therapeutic targets. The user may send a query to the system, e.g., "genes involved in lung cancer". The system may include a first set of terms, set A, which comprises genes that are known to be involved in the formation and progression of lung cancer. Using the adaptive weighting techniques provided herein, the system may analyze a second set of terms, set B, to identify genes predicted to be involved in the formation and progression of lung cancer. By including known entities (e.g., known genes involved in the progression and development of lung cancer in set B), the true relationship between the sets can better be established.

In some aspects, entities from set B appear in a ranked result list between entities in set S known to be related to the query. For example, for the ranked list: (1) entity in set S; (2)

entity in set S; (3) entity in set B; (4) entity in set S, the third entry is located in between set S, and therefore, is predicted to be associated with lung cancer. The third entry may be of particular interest, as this entity has a similarity score and/or ranking flanked by entities having a known relationship to the query.

Predictions may be tested experimentally, and the results of the prediction provided to the cognitive system 60, in order to continually improve and refine predictive abilities. For example, if validated, the entity in set B may be added to set A, for genes involved in lung cancer.

Present invention embodiments may be utilized as part of a cognitive system, e.g., comprising a machine learning system and/or a natural language processing system that is used to extract data (e.g., extract text describing characteristics of an entity, extract drug related information describing characteristics of an entity, and extract chemical information describing structural aspects of an entity). The extracted data may be used to compute similarity scores between entities.

Queries may be provided to the cognitive system to make inferences and predictions based on similarity scores. For compound A, chemical similarity may be a better similarity measure than text similarity, and for compound B, text similarity may be a better similarity measure than chemical similarity. Thus, present embodiments adaptively weight similarity scores, as processing scenarios change due to varying inputs and as information describing characteristics of an entity varies, using a common processing framework that utilizes the same processing operations to dynamically adapt the weights of the similarity scores to the inputs.

It will be appreciated that the embodiments described above and illustrated in the drawings represent only a few of the many ways of implementing embodiments for adaptively weighting different types of similarity scores, to facilitate combination of the different types of similarity scores for improved predictive analytics.

It will also be appreciated that the methods provided herein are implemented by a computer as part of a cognitive system.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, cognitive system 60, cognitive system interface 70, etc.). These systems may include any types of monitors and input devices (e.g., keyboard, mouse, voice recognition, etc.) to enter and/or view information.

It is to be understood that the software (e.g., cognitive system 60) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., cognitive system 60) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., predictive analytics, query inputs, set A, set B, set B', set S, feature vectors, individual similarity scores, individual adaptive weighted similarity scores, AAWS scores, ranking, etc.). The database system may be implemented by any number of any conventional or other databases, data stores or storage structures (e.g., files, databases, data structures, data or other repositories, etc.) to store information (e.g., predictive analytics, query inputs, set A, set B, set B', set S, feature vectors, individual similarity scores, individual adaptive weighted similarity scores, AAWS scores, ranking, etc.). The database system may be included within or coupled to the server and/or client systems. The database systems and/or storage structures may be remote from or local to the computer or other processing systems, and may store any desired data (e.g., predictive analytics, query inputs, set A, set B, set B', set S, feature vectors, individual similarity scores, individual adaptive weighted similarity scores, AAWS scores, ranking, etc.).

The present invention embodiments may employ any number of any type of user interface (e.g., Graphical User Interface (GUI), command-line, prompt, etc.) for obtaining or providing information (e.g., predictive analytics, query inputs, set A, set B, set B', set S, feature vectors, individual similarity scores, individual adaptive weighted similarity scores, AAWS scores, ranking, etc.), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The report may include any information arranged in any fashion, and may be configurable based on rules or other criteria to provide desired information to a user (e.g., predictive analytics, query inputs, set A, set B, set B', set S, feature vectors, individual similarity scores, individual adaptive weighted similarity scores, AAWS scores, ranking, etc., etc.).

The present invention embodiments are not limited to the specific tasks or algorithms described above, but may be utilized for any system in which a combination of individual scores are to be combined, based upon variable input sets of data.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A system for processing a query based on adaptively weighting different types of similarity scores to generate an aggregate adaptively weighted similarity score, the system comprising at least one processor configured to:

receive the query requesting entities related to a subject;

select, in a random manner, one or more entities from a first set of entities that have a known relationship to the subject to form a subset of entities;

combine the subset of entities from the first set of entities with a second set of entities that have an unknown relationship to the first set of entities to produce a combined set of entities;

determine at least two different measures of similarity between each entity in the combined set of entities and the first set of entities;

adjust the combined set of entities until the measures of similarity converge to a given value by:

determining a statistical metric indicating convergence of each measure of similarity to the given value for the combined set of entities; and in response to determining that one or more of the measures of similarity have not converged to the given value based on the statistical metric, selecting a different subset of entities from the first set of entities to form the combined set of entities;

assign, for each entity in the combined set of entities, a weight adaptively to each of the at least two different measures of similarity for that entity based on a respective magnitude of each measure of similarity, wherein the weight for each measure of similarity for each entity in the combined set of entities is computed from the at least two different measures of similarity for that entity, and wherein weights for the at least two different measures of similarity dynamically change among the entities of the combined set of entities as the magnitudes of the at least two different measures of similarity change;

apply each adaptively assigned weight to a corresponding measure of the at least two different measures of similarity for each entity in the combined set of entities to produce weighted measures of similarity for that entity;

combine the weighted measures of similarity for each entity of the combined set to determine an aggregate weighted similarity score for each entity of the combined set; and produce results for the query including a list of entities of the combined set ranked according to the aggregate weighted similarity score, wherein ranking of entities in the list reflects a likelihood an entity in the list shares the known relationship of the first set.

2. The system of claim 1, wherein the measures of similarity include two or more from a group of a text-based similarity, a chemical similarity, and a drug similarity.

3. The system of claim 1, wherein adaptive weights assigned to the measures of similarity are normalized.

4. The system of claim 1, wherein the at least one processor is further configured to assign, for each entity in the combined set of entities, the weight adaptively to each of the at least two different measures of similarity for that entity based on the respective magnitude of each measure of similarity by determining for two measures of similarity which measure of similarity has a highest respective magnitude among the two measures of similarity and assigning α weight α to this measure of similarity, and assigning a weight of 1-α to the other measure of similarity.

5. The system of claim 1, wherein the at least one processor is further configured to assign, for each entity in the combined set of entities, the weight adaptively to each of the at least two different measures of similarity for that entity by assigning a weight in response to the respective magnitude of each measure of similarity, which is determined in part by specific entities of the subset.

6. The system of claim 1, wherein the at least two different measures of similarity include three or more different measures of similarity and the first set of entities includes a plurality of different subsets, and the at least one processor is further configured to:
  omit a measure of similarity from the at least two different measures of similarity in response to that measure of similarity not converging to the given value after processing combined sets formed from the second set of entities and the plurality of different subsets.

7. A computer program product for processing a query based on adaptively weighting different types of similarity scores to generate an aggregate adaptively weighted similarity score, the computer program product comprising one or more computer readable storage media collectively having program instructions embodied therewith, the program instructions executable by a processor to:
  receive the query requesting entities related to a subject;
  select, in a random manner, one or more entities from a first set of entities that have a known relationship to the subject to form a subset of entities;
  combine the subset of entities from the first set of entities with a second set of entities that have an unknown relationship to the first set of entities to produce a combined set of entities;
  determine at least two different measures of similarity between each entity in the combined set of entities and the first set of entities;
  adjust the combined set of entities until the measures of similarity converge to a given value by:
    determining a statistical metric indicating convergence of each measure of similarity to the given value for the combined set of entities; and
    in response to determining that one or more of the measures of similarity have not converged to the given value based on the statistical metric, selecting a different subset of entities from the first set of entities to form the combined set of entities;
  assign, for each entity in the combined set of entities, a weight adaptively to each of the at least two different measures of similarity for that entity based on a respective magnitude of each measure of similarity, wherein the weight for each measure of similarity for each entity in the combined set of entities is computed from the at least two different measures of similarity for that entity, and wherein weights for the at least two different measures of similarity dynamically change among the entities of the combined set of entities as the magnitudes of the at least two different measures of similarity change;
  apply each adaptively assigned weight to a corresponding measure of the at least two different measures of similarity for each entity in the combined set of entities to produce weighted measures of similarity for that entity;
  combine the weighted measures of similarity for each entity of the combined set to determine an aggregate weighted similarity score for each entity of the combined set; and
  produce results for the query including a list of entities of the combined set ranked according to the aggregate weighted similarity score, wherein ranking of entities in the list reflects a likelihood an entity in the list shares the known relationship of the first set.

8. The computer program product of claim 7, wherein the measures of similarity include two or more from a group of a text-based similarity, a chemical similarity, and a drug similarity.

9. The computer program product of claim 7, wherein adaptive weights assigned to the measures of similarity are normalized.

10. The computer program product of claim 7, wherein the program instructions are executable to assign, for each entity in the combined set of entities, the weight adaptively to each of the at least two different measures of similarity for that entity by assigning a weight in response to the respective magnitude of each measure of similarity, which is determined in part by specific entities of the subset.

11. The computer program product of claim 7, wherein the program instructions are executable to assign, for each entity in the combined set of entities, the weight adaptively to each of the at least two different measures of similarity for that entity based on the respective magnitude of each measure of similarity by determining for two measures of similarity which measure of similarity has a highest respective magnitude among the two measures of similarity and assigning a weight $\alpha$ to this measure of similarity, and assigning a weight of $1-\alpha$ to the other measure of similarity.

12. The computer program product of claim 7, wherein the at least two different measures of similarity include three or more different measures of similarity and the first set of entities includes a plurality of different subsets, and the program instructions are further executable by the processor to:
  omit a measure of similarity from the at least two different measures of similarity in response to that measure of similarity not converging to the given value after processing combined sets formed from the second set of entities and the plurality of different subsets.

* * * * *